(12) United States Patent
Cho et al.

(10) Patent No.: US 7,321,654 B2
(45) Date of Patent: Jan. 22, 2008

(54) NARROW BAND X-RAY SYSTEM AND FABRICATION METHOD THEREOF

(75) Inventors: Yong Min Cho, Silver Spring, MD (US); Daesoo Han, Sandy Spring, MD (US)

(73) Assignee: Mentor Technologies, Inc., Lanham, MD (US)

( * ) Notice: Subject to any disclaimer, the term of this patent is extended or adjusted under 35 U.S.C. 154(b) by 4 days.

(21) Appl. No.: 10/857,927

(22) Filed: Jun. 2, 2004

(65) Prior Publication Data

US 2005/0281384 A1 Dec. 22, 2005

Related U.S. Application Data

(60) Provisional application No. 60/651,460, filed on Jun. 3, 2003.

(51) Int. Cl.
*G21K 3/00* (2006.01)
(52) U.S. Cl. .................. 378/158; 378/156; 378/157
(58) Field of Classification Search .................. 378/16, 378/156–159; 359/584–590, 592–598
See application file for complete search history.

(56) References Cited

U.S. PATENT DOCUMENTS

| | | | | | |
|---|---|---|---|---|---|
| 4,519,503 | A | * | 5/1985 | Wilson | 206/505 |
| 4,969,175 | A | * | 11/1990 | Nelson et al. | 378/146 |
| 5,016,267 | A | * | 5/1991 | Wilkins | 378/84 |
| 5,086,443 | A | * | 2/1992 | Bloch et al. | 378/145 |
| 5,406,609 | A | | 4/1995 | Arai et al. | |
| 5,744,813 | A | * | 4/1998 | Kumakhov | 250/505.1 |
| 6,271,534 | B1 | * | 8/2001 | Kumakhov | 250/505.1 |
| 6,278,764 | B1 | * | 8/2001 | Barbee et al. | 378/84 |
| 6,529,578 | B1 | | 3/2003 | Taguchi et al. | |
| 6,624,431 | B1 | * | 9/2003 | Foster et al. | 250/505.1 |
| 6,678,348 | B1 | | 1/2004 | Kumakhov | |
| 2001/0028699 | A1 | * | 10/2001 | Iwasaki | 378/84 |
| 2003/0128810 | A1 | | 7/2003 | Verman et al. | |
| 2005/0220271 | A1 | * | 10/2005 | Cho | 378/156 |

OTHER PUBLICATIONS

NASA Chandra X-ray Telescope Fact Sheet: from http://web.archive.org/web/20021010032838/www1.msfc.nasa.gov/NEWS-ROOM/background/facts/axaf.html, which is the Way Back Machine's (http://web.archive.org) entry for http://chandra.nasa.gov/ as of Dec. 8, 2002 (see http://web.archive.org/web/*/http://chandra.nasa.gov/).

(Continued)

*Primary Examiner*—Edward J. Glick
*Assistant Examiner*—Anastasia S. Midkiff
(74) *Attorney, Agent, or Firm*—Harness, Dickey & Pierce, PLC

(57) ABSTRACT

A narrow band x-ray filter can include: a substrate; and a sheaf of one or more reflection units stacked upon each other on the substrate. Each reflection unit can include: a first set of at least two discrete spacers on a respective underlying structures, a reflector disposed on the first set of spacers so as to form a void between the respective underlying structure and the reflector; and a first set of at least two discrete shims disposed on the first set of at least two spacers, each shim being at least substantially the same thickness as the reflector. A first device to produce a narrow band x-ray beam may include such a filter or an x-ray telescope. A second device to make an x-ray image of a subject may include the first device.

24 Claims, 10 Drawing Sheets

OTHER PUBLICATIONS

"The Swift X-Ray Telescope," David N. Burrows et al., SPIE, San Diego, Aug. 2, 2000, downloaded from http://www.swift.psu.edu/xrt/posters/2000_SPIE_xrt.ppt.

Chandra X-Ray Telescope Brochure, May 2000, Chandra Specifications, from http://chandra.harvard.edu/resources/handouts/lithos/chandra_specs_litho.pdf.

Illuminating Geometry from http://www.google.com/search?q=reverse+telescope&hl=en&lr=&start=20&sa=N.

Re: ATM camera lens eyepiece from http://astro.umsystem.edu/atm/ARCHIVES/APR01/msg00994.html.

Clinical and Experimental Optometry 84.3 May 2001 pp. 162-164—Original Paper, Determining the power of a negative lens field expander, George C. Woo OD PhD, Brian Ing OD, Man-ho Lee BSc (Hons).

International Search Report for PCT/US04/17131 dated Jan. 17, 2006.

Written Opinion of the International Searching Authority for PCT/US04/17131 dated Jan. 17, 2006.

"X-ray monochromator for divergent beam radiography using conventional and laser produced X-ray sources," H.W. Schnopper, S. Romaine, and A. Krol, *Proceedings of SPIE*, vol. 4502, No. 24, 2001, pp. 19-29.

"Masked deposition techniques for achieving multilayer period variations required for short-wavelength (68Å) soft-x-ray imaging optics," J.B. Kortright, E.M. Gullikson, and P.E. Denham, *Applied Optics*, Optical Society of America, vol. 32, No. 34, Dec. 1, 1993, pp. 6961-6968.

"Development of Thermally Formed Glass Optics for Astronomical Hard X-ray Telescopes," W. Craig et al., *Optics Express*, vol. 7, No. 4, Aug. 14, 2000, pp. 178-185.

"Development and production of hard X-ray multilayer optics for HEFT," J.E. Koglin et al., *Proceedings of SPIE*, vol. 4851, 2003, pp. 607-618.

"Development of precision hard X-ray multilayer optics with sub-arcminute performance," J.E. Koglin et al, *Proceedings of SPIE*, vol. 4851, 2003, pp. 673-683.

"Fabrication and Performance of Constellation-X Hard X-ray Telescope Prototype Optics Using Segmented Glass," C.J. Hailey et al., *Proceedings of SPIE*, vol. 5168, 2004, pp. 90-99.

"X-ray and far UV multilayer mirrors: principles and possibilities," A.V. Vinogradov and B. Ya. Zeldovich, *Applied Optics*, vol. 16, No. 1, Jan. 1977, pp. 89-93.

Spiller, Eberhard, *Soft X-ray Optics*, SPIE Optical Engineering Press, Bellingham, 1994, pp. 139-168, also v-viii and 275-278.

PCT International Search Report (PCT Article 18 and Rules 43 and 44) dated Feb. 1, 2007, for corresponding PCT Application No. PCT/US06/19602.

R.J. Harms, P.J. Serlemitsos, S.M. Owens; Thin Film Multilayer Fan-Beam X-Ray Monochromator.

International Search Report for PCT/US04/17131 dated Jan. 17, 2006.

Written Opinion of the International Searching Authority for PCT/US04/17131 dated Jan. 17, 2006.

* cited by examiner (cross-section IIIA-IIIA')

(top view)

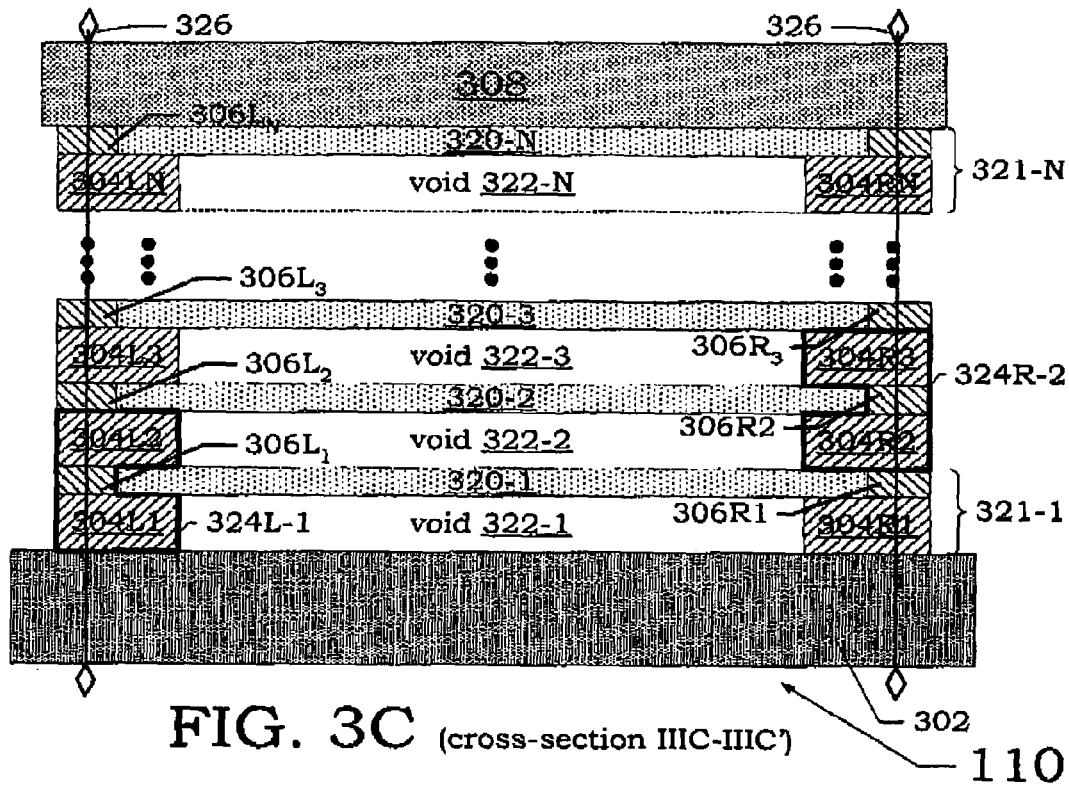
FIG. 3C (cross-section IIIC-IIIC')
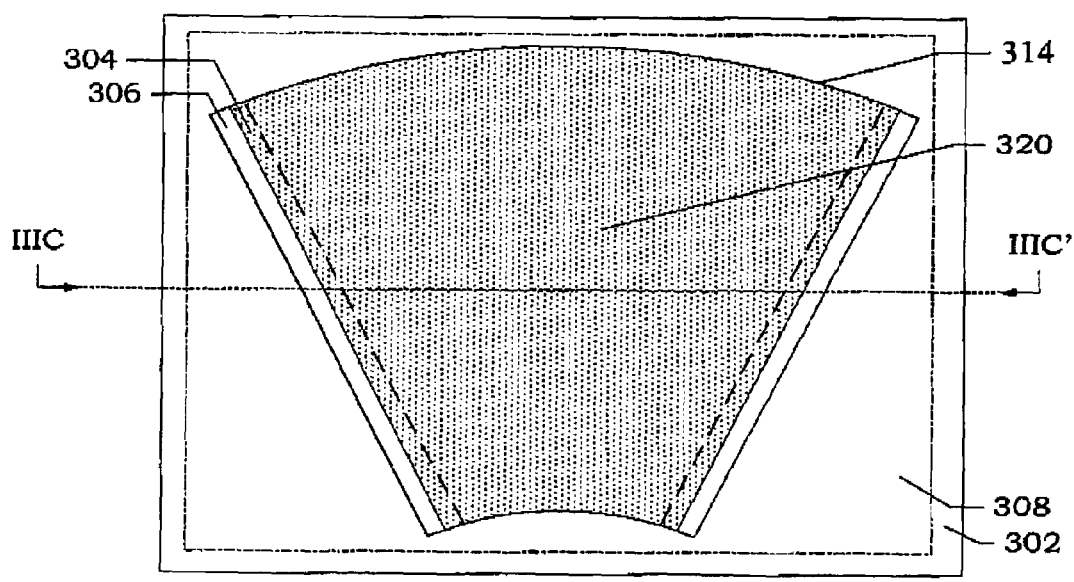
FIG. 3D (top view)

320

NARROW BAND X-RAY SYSTEM AND FABRICATION METHOD THEREOF

PRIORITY INFORMATION

This application claims priority upon provisional U.S. patent application having Ser. No. 60/651,460, filed Jun. 3, 2003, for which priority is claimed under 35 U.S.C. 119(e), and the disclosure of which is incorporated herein in its entirety.

BACKGROUND OF THE PRESENT INVENTION

Systems are known in the Background Art which make an x-ray image of a subject (x-ray radiology) for the purposes, e.g., of obtaining medical diagnostic information about a living organism, obtaining security assessment information about an inanimate object and/or a living organism, etc. Such systems use a broad band x-ray beam.

It has long been recognized in the Background Art that medical diagnostic x-ray radiology using a narrow band x-ray beam would be desirable. The center frequency of such a narrow band would be varied in dependence upon the circumstances in which use of the medical diagnostic x-ray radiology arises.

A prototype has been proposed in the Background Art of a filter to produce a narrow band beam of divergent x-rays from a wide band x-ray beam, for use with a medical x-ray diagnostic system. The filter is interposed between a source (located substantially at the focal point of the filter) of the wide band x-ray beam and an x-ray detector. A subject for which an x-ray image is to be made is interposed between the filter and the detector.

The Background Art filter uses a plurality of mirrors arranged in a manner that resembles an annular segment of a slide-carousel having film slides disposed therein. As such, the mirrors are vertically oriented but not in parallel planes, rather the planes of the mirrors are divergent. Together, the mirrors have a fan-shaped silhouette when viewed from above. Complimentary upper and lower frames hold the mirrors in this arrangement. The frames each are integral units into which grooves are cut, the mirrors being lodged in the grooves.

Also, telescopes tuned to x-ray frequencies, or in other words x-ray telescopes, are known in the Background Art. While manufactured on Earth, x-ray telescopes have been used only in outer space.

SUMMARY OF THE PRESENT INVENTION

At least one embodiment of the present invention provides a narrow band x-ray filter. Such a filter may include: a substrate; a sheaf of one or more reflection units stacked upon each other on the substrate, each reflection unit including a first set of at least two discrete spacers on a respective underlying structure, a reflector disposed on the first set of spacers so as to form a void between the respective underlying structure and the reflector, and a first set of at least two discrete shims disposed on the first set of at least two spacers, each shim being at least substantially the same thickness as the reflector.

At least one embodiment of the present invention provides a first apparatus to produce a substantially narrow band x-ray beam. Such an apparatus may include: a source of a first x-ray beam; and a narrow band x-ray filter having a first end, a second end and a focal point located nearer to the first end than to the second end, the source being disposed substantially at the focal point such that a substantially narrow band x-ray beam emanates from the second end of the filter, and a cross-section of the narrow band x-ray beam corresponding to at least a majority of the cross-section of the first x-ray beam.

At least one embodiment of the present invention provides a second apparatus to produce a substantially narrow band x-ray beam. Such an apparatus may include: an x-ray telescope; and a source of x-rays located substantially at a focal point of the telescope near a first end thereof such that a substantially narrow band beam of parallel x-rays emanates from a second end of the telescope.

At least one embodiment of the present invention provides a third apparatus to make an x-ray image of a subject. Such an apparatus may include: the first apparatus, mentioned above, to produce a substantially narrow band x-ray beam; and an x-ray detector arranged to receive the narrow band x-ray beam so that a subject disposed between the second end of the filter and the detector casts an image thereon.

At least one embodiment of the present invention provides a fourth apparatus to make an x-ray image of a subject. Such an apparatus may include: the second apparatus, mentioned above, and an x-ray detector arranged to receive the narrow band x-ray beam so that a subject disposed between the second end of the telescope and the detector casts an image thereon.

At least one embodiment of the present invention provides a method of making a narrow band x-ray filter. Such a method may include: providing a substrate; and stacking one or more reflection units in succession upon the substrate.

Additional features and advantages of the present invention will be more fully apparent from the following detailed description of example embodiments, the accompanying drawings and the associated claims.

BRIEF DESCRIPTION OF THE DRAWINGS

The above and other aspects and advantages of the present invention will become more apparent by describing in detail example embodiments thereof with reference to the attached drawings in which:

FIGS. 3A-3D are more detailed depictions of the filter of FIG. 1, according to at least one embodiment of the present invention;

FIG. 8A is a simplified perspective side view of the Background Art narrow band x-ray filter, while FIG. 8C is a simplified perspective side view of narrow band the x-ray filter of FIGS. 3A-3D, while

DETAILED DESCRIPTION OF THE PRESENT INVENTION

The present invention will be described more fully with reference to the accompanying drawings, in which example embodiments of the present invention are shown. It should be understood, however, that example embodiments of the present invention described herein can be modified in form and detail without departing from the spirit and scope of the present invention. Accordingly, the embodiments described herein are provided by way of example and not of limitation, and the scope of the present invention is not restricted to the particular embodiments described herein.

In particular, the relative thicknesses and positioning of layers or regions may be reduced or exaggerated for clarity. In other words, the figures are not drawn to scale. Further, a layer is considered as being formed "on" another layer or a substrate when formed either directly on the referenced layer or the substrate or formed on other layers or patterns overlaying the referenced layer.

In developing embodiments of the present invention, the following problem with the Background Art was recognized, its physics assessed and a path to a solution identified. While of simple construction, the narrow band x-ray filter prototype according to the Background Art is difficult to manufacture. The upper and lower frames are each integral members that must be precisely disposed apart from one another in a fixed relationship, after which the mirrors must be slid individually therebetween into the corresponding grooves of the upper and lower frames. Alternatively, all of the mirrors must be set in the lower frame and precisely vertically aligned, after which the upper frame is lowered onto the mirrors such that the mirrors become lodged in the grooves of the upper frame. Both methods are tedious, slow, and prone to damaging the mirrors and/or the frames. A multi-mirror filter having upper & lower (or left & right) frames built up from discrete components rather than being formed of one integral component could facilitate less tedious, faster and low damage manufacture of such a filter. At least one embodiment of the present invention provides such a filter.

Figure 1:
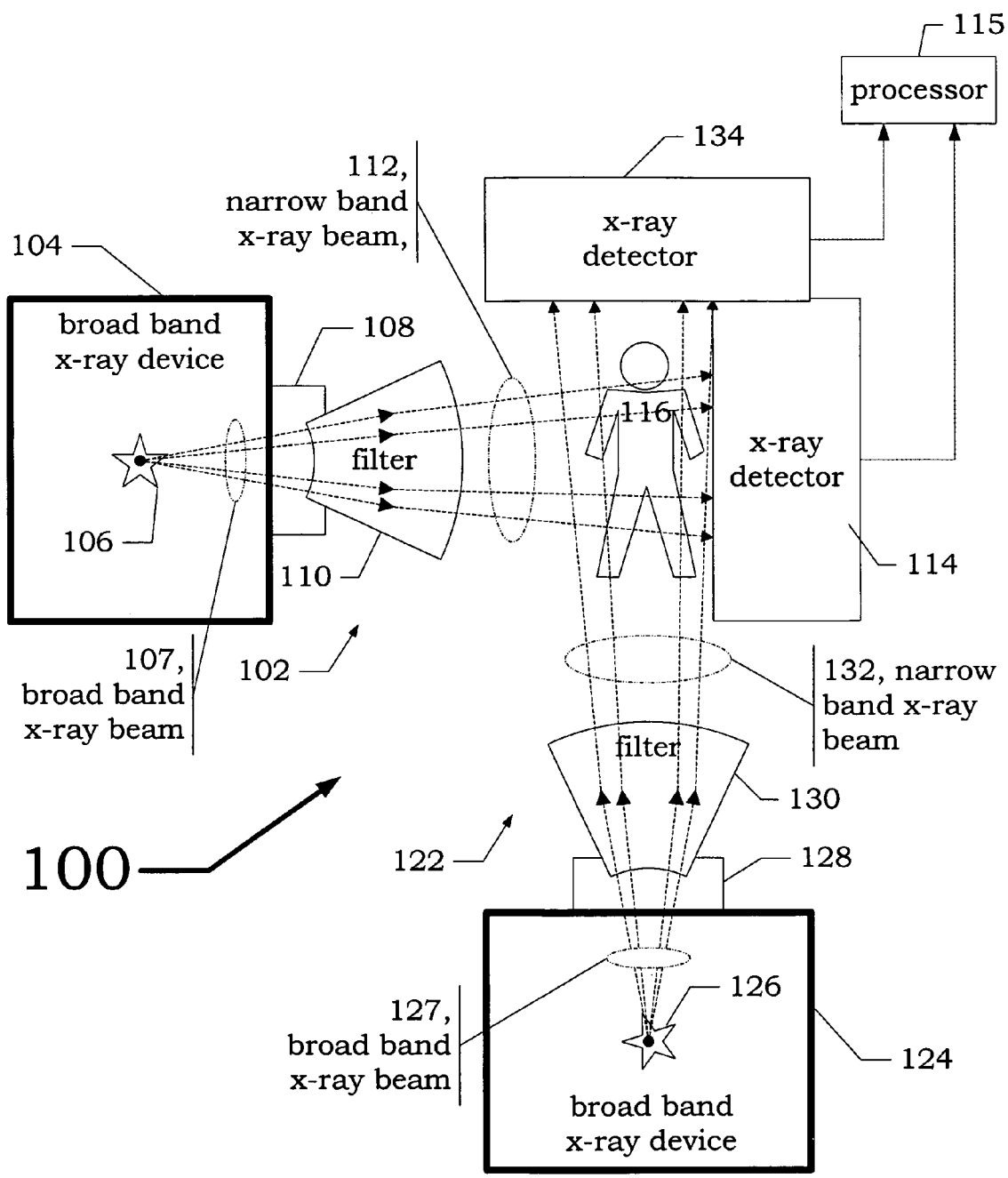
FIG. 1 is a block diagram of an x-ray radiology system according to at least one embodiment of the present invention.

FIG. 1 is a block diagram of an x-ray radiology system 100 according to at least one embodiment of the present invention. The system 100 includes: a source 104 of a broad band beam 107 of x-rays that itself includes an anode 106 from which the broad band x-ray beam 107 is emitted; a narrow band x-ray filter 110; an alignment mechanism 108; and an x-ray detector 114.

As used herein, the term "narrow band x-ray beam" is to be understood as at least a quasi-mono-energetic, spatially extended beam of x-rays, if not a substantially mono-energetic beam of x-rays.

Construction of filter 110 and alignment mechanism 108 are discussed below. Source 104 and detector 114 are known. For example, source 104 can be the x-ray emitting portion of an x-ray radiology device according to the Background Art. Similarly, for example, detector 104 can be either known x-ray film or an x-ray-to-charge converter, e.g., a charge-coupled display (CCD). In the latter case of a CCD, a processor 115 would be included to harvest and process data from CCD 134 in a known manner to form an x-ray image.

Passage of broad band beam 107 through narrow band filter 110 produces a narrow band beam 112 of x-rays. Relative to anode 106, alignment mechanism 108 moves filter 110 in at least one and up to three degrees of freedom. Alignment mechanism 108 is constructed, and operates, very similarly to a lens of a camera. In a camera, the optical elements are adjusted (either manually or via one or more motors) in typically one dimension to move the focal point of the lens (via movement of the lens) onto a photographic film surface or the surface of a solid-state imager that (relative to the movable lens) has a fixed position in space. In system 100, alignment mechanism 108 is used to precisely align a focal point of filter 110 onto anode 106 in 1-3 dimensions. In other words, anode 106 has a fixed location in space relative to filter 110, which is movable via alignment mechanism 108.

In FIG. 1, a subject 116 of the x-ray radiology, e.g., a living organism such as a person, is interposed between filter 110 and detector 114 so that narrow band x-ray beam 112 impinges on subject 116. Varying attenuation of narrow band x-ray beam 112 by different parts of subject 116 cast an x-ray shadow of varying intensities onto detector 114, which detector 114 converts into an image of subject 116. Alternatively, subject 116 can be some other genus and species of living organism, or an inanimate object, e.g., a package, a piece of luggage, etc.

In FIG. 1, the x-rays that comprise narrow band beam 112 diverge away from filter 110. Such divergence causes a shadow vast by subject 116 to be magnified. To reduce such magnification (and therefore improve the accuracy of the resulting image), subject 116 should be positioned as closely to detector 114 as possible.

In FIG. 1, item nos. 104-115 can be considered a subsystem 102. A variation of system 100 can include an optional second subsystem 122 that corresponds to subsystem 102 and has optional similar components 124-134, respectively. Subsystem 122 is arranged orthogonally to subsystem 102, which can reduce or eliminate the need to change the position of the subject 116 otherwise associated with using only subsystem 102.

Figure 2:
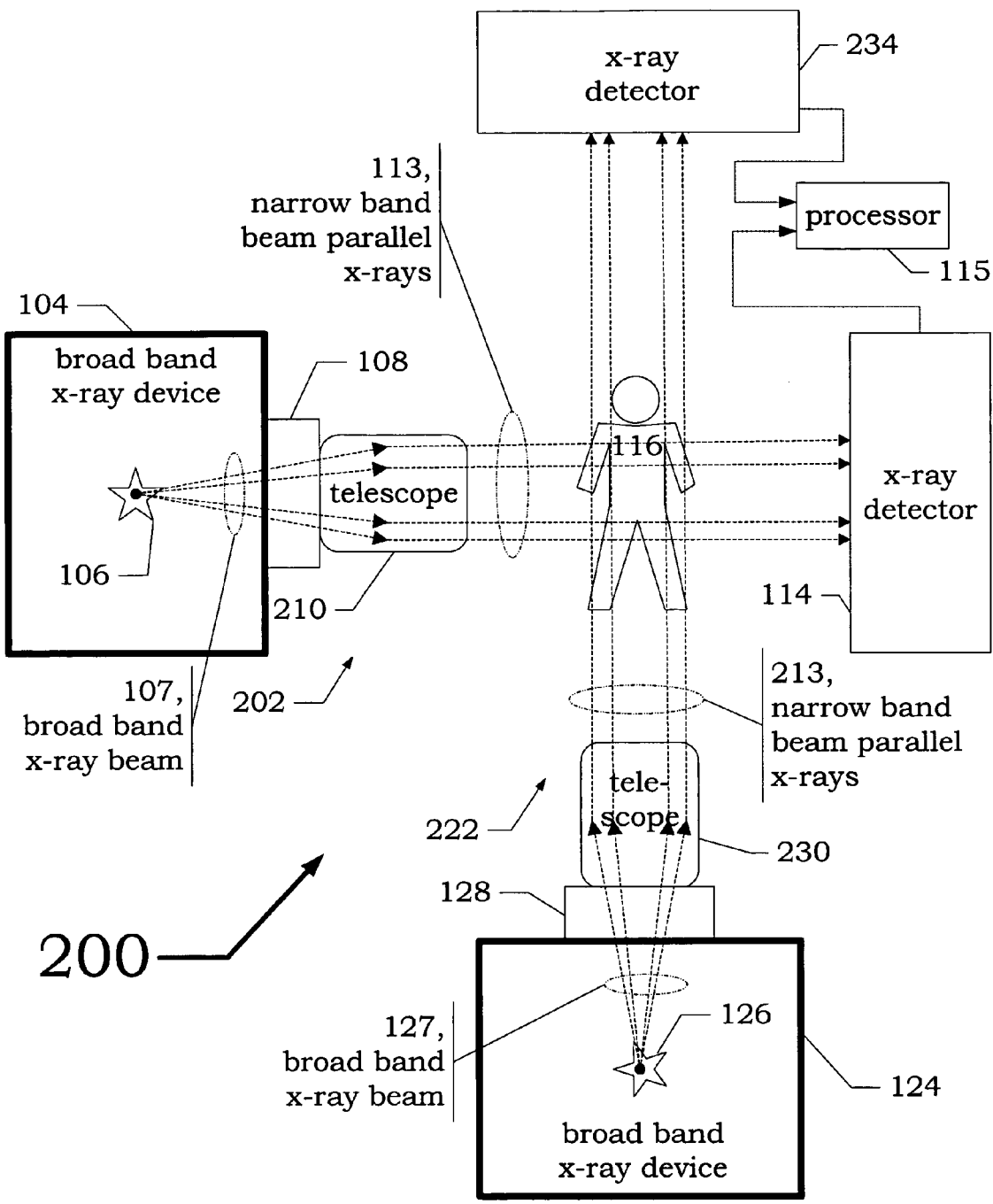
FIG. 2 is a block diagram of an x-ray radiology system according to at least one embodiment of the present invention.

FIG. 2 is a block diagram of an x-ray radiology system 200 according to at least one embodiment of the present invention. The system 200 is very similar in some respects to system 100, as reflected by certain components sharing the same reference number. System 200 includes: source 104 (via anode 106) of broad band x-ray beam 107; alignment mechanism 108; and x-ray detector 114. Instead of filter 110, system 200 includes an x-ray telescope 210. X-ray teloscopy, including the design and construction of x-ray telescopes, is known.

Like filter 110, telescope 210 produces a narrow band beam 113 of x-rays. But while beam 112 (produced by filter 110) has divergent x-rays, beam 113 (produced by telescope 210) is comprised of at least substantially parallel x-rays. A benefit from beam 113 being formed of at least substantially parallel x-rays is that the shadow cast by subject 116 is subject to little if any magnification. Hence, subject 116 need not be located closely adjacent detector 114. Such a benefit comes at the cost of telescope 210 being larger than filter 110.

In terms of a linear path between anode 106 and detector 114, an example of the portion represented by the body (body length, Lb) of telescope 210 can be about 10 inches, while a thickness or diameter (DB) of telescope 210 can be about 12 inches. Continuing the example, a portion of the path represented by the focal length (Lf) of telescope 210 (or, in other words, the distance between anode 106 and telescope 210) can be about 2-5 meters. In general, $$Lf=f(DB,Lb) \quad (1)$$

An additional benefit of system 200 arising from the parallel nature of the x-rays in beam 113 is that subject 116 receives a substantially uniform dosage of x-rays across his body.

In FIG. 2, item nos. 104-108, 210 and 113-115 can be considered a subsystem 202. A variation of system 200 can include an optional second subsystem 222 that corresponds to subsystem 202 and has optional similar components 124-128, 230 and 233-234, respectively. Subsystem 222 is arranged orthogonally to subsystem 202, which can reduce or eliminate the need to change the position of the subject 116 otherwise associated with using only subsystem 102.

Figure 3A:
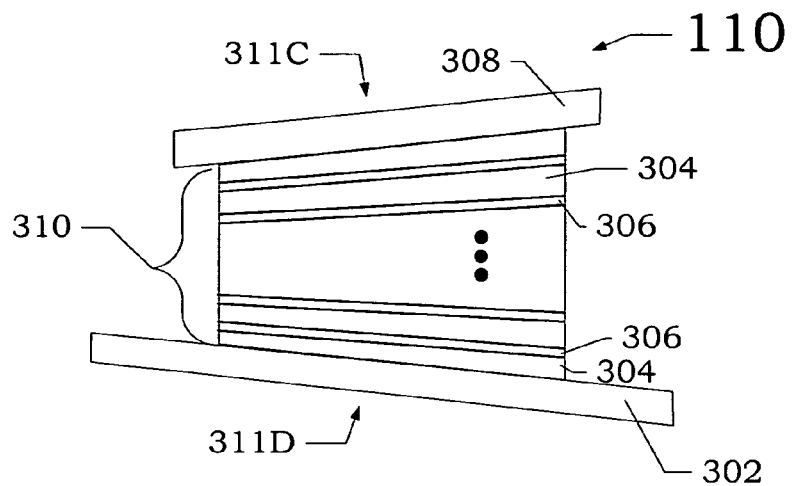
Figure 3B:
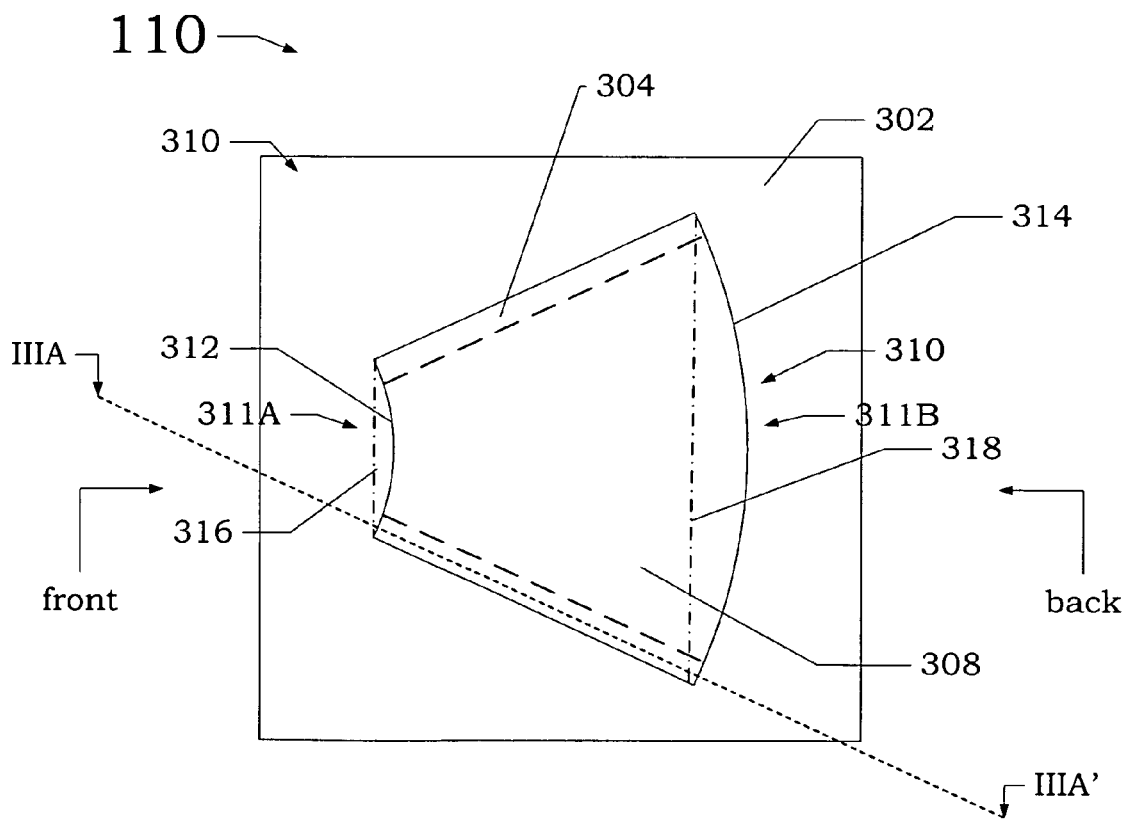

FIGS. 3A-3D are more detailed depictions of fitter 110, according to at least one embodiment of the present invention. FIG. 3B is a top view of filter 110. FIG. 3A is a cross-sectional view of filter 110 taken along line IIIA-IIIA' of FIG. 3B. FIG. 3D is a more-detailed top view of filter 110 in which the depiction of filter 110 is rotated counterclockwise 90° relative to FIG. 3B. And FIG. 3C is a cross-sectional view of filter 110 taken along line IIIC-IIIC' of FIG. 3D.

In FIG. 3A, filter 110 is depicted as including: a base 302; angled spacers 304; shims 306; and a top member 308. Base 302, spacers 304 and shims 306 can be made, e.g., of aluminum (Al) or a similar metal, or another material of suitable manufacturing qualities and suitable x-ray telescopy qualities.

As seen in FIG. 3A, a first spacer 304 is placed on base 302. A first shim is placed on the first spacer 304. A second spacer 304 is placed on the first shim 306. A second shim 306 is placed on the second spacer 304. Such an alternating pattern of spacer 304 and shim 306 is repeated until a sufficient number of spacer/shim pairs has been built up. Then top member 308 is disposed on the uppermost shim 306. As will be discussed below, edges of reflectors are disposed in recesses formed by a triplet of two spacers 304 and a shim 306. Spacers 304 and shims 306 are bounded between top member 308 and base 302 so as to form a sheaf 310 of reflectors.

Two shapes in FIG. 3A are to be noted. Overall, the side silhouette of sheaf 310 (as viewed from left to right in FIG. 3A) is fan-shaped or trapezoidally-shaped ed (with the smaller end of the trapezoid being arranged to the left of FIG. 3A and the bigger end being arranged toward the right of FIG. 3A). Similarly, each of spacers 304 is trapezoidally-shaped in a similar manner to the silhouette of sheaf 310, although the taper of spacer 304 is not as great as the taper of sheaf 310. In other words, the upper and lower surfaces of spacer 304 are less divergent than the upper and lower surfaces of sheaf 310. In contrast, base 302, shims 306 and top member 308 can have parallel, or substantially parallel, upper and lower surfaces. Also, upper edge 311C and bottom edge 311D diverge towards right side 311B and away from left side 311A.

In FIG. 3B, which again is a top view of filter 110, the top silhouette of sheaf 310 (as viewed from left to right in FIG. 3B) also is generally fan-shaped or trapezoidally-shaped.

The smaller end of the trapezoid is arranged to the left side 311A of FIG. 3B and the bigger end is arranged toward the right side 311B of FIG. 3B. More particularly, the top silhouette of sheaf 310 can be described as an annular segment because a front surface 312 and a back surface 314 of sheaf 310 can be substantially circular arc-segments, respectively, where front surface 312 represents a smaller arc-segment than back surface 314. As an alternative, front surface 312 and back surface 314 can be configured as substantially planar surfaces, which is indicated by dashed straight lines 316 and 318, respectively.

In FIG. 3C, which again is a cross-sectional view of filter 110 taken along line IIIC-IIIC' of FIG. 3D, a first pair of spacers (or rails) 304L1 and 304R1 are disposed on base 302. Reflector 320-1 is disposed on spacers 304L1 and 304R1, which defines a void 322-1. Void 322-1 is bounded by reflector 320-1, spacers 304L1 and 304R1, and base 302.

Spacers 304L2 and 304R2 are disposed over side ends of reflector 320-1 and over spacers 304L2 and 304R1. Typically, a reflector 320 is not a structural element and thus cannot withstand significant compression. Accordingly, shims 306 are in general disposed on spacers 304 adjacent to or abutting side edges of reflector 320, and are constructed to be at least the same thickness as reflector 320. To ensure a snug fit without play between spacers 304 and reflector 320, shims 306 should not be of much greater thickness than reflector 320 unless some other shims or packing are provided to reduce the play. Shims $306L_1$ and $306R_1$ can be considered parts of the rails that include spacers 304L1 and 304R1, respectively. Taken together, for example, spacer 304L1 and shims $306L_1$ can be described as having a stepped appearance or representing a stepped portion. Alternatively, spacer 304L1 and shims $306L_1$ can be described as portion of a base including a staircase having two or more steps.

In particular, shims 306L1 and 306R1 are disposed adjacent to or abutting side edges of reflector 320-1 and on spacers 304L1 and 304R1. Spacers 304L2 and 304R2 are disposed on spacers 304L2 and 304R1.

In dependence upon the materials from which reflector 320 is constructed, spacers 304L-2 and 304R-2 might be in direct contact with reflector 320-1 due to shims 306L-1 and 306R-1 being the same (or substantially the same) thickness as reflector 320-1. Alternatively, shims 306L-1 and 306R-1 can be slightly thicker than reflector 320-1 in order to reduce compression stress upon reflector 320-1 caused by spacers 304L-2 and 304R-2.

As introduced above, the two spacers 304L-1 & 304L-2 and shim 306L-1 form a triplet, or recess arrangement, 324L-1 into which a left side edge of reflector 320-1 is inserted. A corresponding triplet 324R-1 is comprised of the two spacers 304R-1 & 304R-2 and shim 306R-1. In general, for each reflector 320-(i), there will be a corresponding left-edge triplet 324Li comprised of spacers 304L(i) & 304L-(i+1) and shim 306L-(i), and a corresponding right-edge triplet 324Ri comprised of spacers 304R-(i) & 304R-(i+1) and shim 306R-(i).

A reflection unit 321-i includes: spacers 304L-i and 304R-i; shims 306L-i and 306R-i; and reflector 320-i. In combination with the underlying structure, reflection unit 321-i defines void 322-i. With the exception of reflection unit 321-1, the underlying structure for reflection unit 321-(i+1) will be reflector 320-i. For reflection unit 321-1, the underlying structure (again) is base 302. Recalling FIG. 3A, there corresponding shims 306 and spacers 304 represent reflection units. Also there, the reflection units can be described as being aligned according to a plurality of radial planes that share a common origin (not depicted). For example, filter 110 can be disposed so that source 106 is located at the common origin.

In FIG. 3C, a total of N reflection units are shown. Top member 308 is disposed on reflection unit 321-N, e.g., to impart rigidity to filter 110 as a whole. Any number of reflection units 321 can be stacked together, e.g., 2-300. To improve mechanical stability of the stack of reflection units 321, a binding mechanism 326 can be arranged at the side edges of filter 110 to prevent reflection units 321 from becoming unstacked.

Binding mechanism 326 can take a variety of forms. For example, binding mechanism 326 can be a nut & bolt arrangement that compresses top member 308 and base 302 towards each other, which compresses intervening spacers 304 and shims 306 together. A similar effect can be achieved, e.g., where binding mechanism 326 takes the form of a clamp assembly that clamps against top member 308 and base 302, etc., or a screw having a head the bears against top member 308 and threads that bite into base 302 or vice-versa. Furthermore, a similar effect can be obtained by binding base 302, spacers 304, shims 306 and top member 308 respectively together with an adhesive. In the nut & bolt, screw and some forms of the clamp approach, a hole is formed in top member 308 (at least partially depending upon the approach), the underlying stack of spacers 304 and shims 306, and base 302 (similarly, at least partially depending upon the approach).

In FIG. 3D, which again is a more-detailed top view of filter 110 (rotated counterclockwise 90° relative to the depiction of filter 110 in FIG. 3B), reflector 320 is depicted with stippling to draw attention to its arrangement relative to spacers 304 and shims 306. Again, side edges of reflector 320 are disposed on portions of spacers 304. Sides of reflector 320 can be adjacent to or abut shims 306. Also, shims 306 can be disposed on other portions of the upper surface of spacers 304 not otherwise occupied by side edges of reflector 320.

The top silhouette of sheaf 310 (as viewed from bottom to top in FIG. 3D) also is generally fan-shaped or trapezoidally-shaped (again, with the smaller end of the trapezoid being arranged towards the bottom of FIG. 3D and the bigger end being arranged towards the top of FIG. 3D). More particularly, the top silhouette of sheaf 310 in FIG. 3D can be described as an annular segment.

Figure 4A:
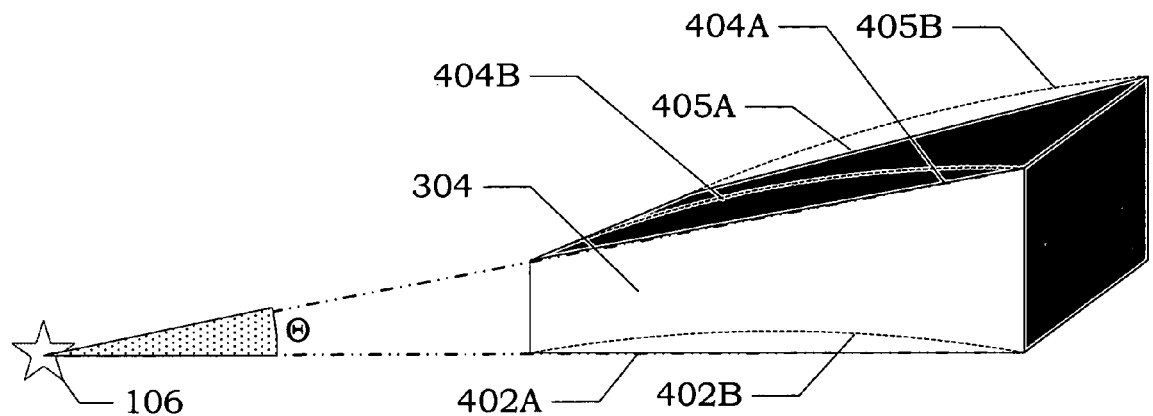
FIG. 4A is a perspective side view of the spacer of FIGS. 3A-3D, according to at least one embodiment of the present invention.

FIG. 4A is a perspective side view of spacer 304, according to at least one embodiment of the present invention. Front bottom edge 402A, front upper edge 404A, rear upper edge 405A and the corresponding rear lower edge (not depicted in FIG. 4A) can be straight (or substantially straight) surfaces where reflector 320 has straight (or substantially straight) side edges. Alternatively, where the side edges of reflector 320 are curved (to be discussed further below), then front bottom edge 402B, front upper edge 404B, rear upper edge 405B and the corresponding rear lower edge (not depicted in FIG. 4A) can take on a corresponding curved configuration.

It is noted that front upper edge 404A & rear upper edge 405A, and separately front bottom edge 402A & the corresponding rear lower edge, can be parallel (or substantially parallel). In contrast, front bottom edge 402A & front upper edge 404A, and separately rear upper edge 405A and the corresponding rear lower edge can be considered as respectively divergent. Moreover, the angle of divergence is θ, as described below in the discussion of FIG. 6.

If curved, then reflector 320 (and corresponding surfaces 402B, 404B, 405B, etc. of spacers 304) should be curved so as to produce substantially the same angle of reflection any point along the curve relative to a fixed location of anode 106. Such a curve is a function of the focal length (Lf, see the discussion below of FIG. 6) and the body length (Lb, again, see the discussion below of FIG. 6) of filter 110. This relation can be stated as follows.

$$\text{curve} = f(Lf, Lb) \tag{2}$$

Software to determine such a curve, and its associated surface of revolution is known, e.g., the Optica model of ray-tracing system that runs on the Mathematica® platform (itself an integration of a numeric and symbolic computational engine, graphics system, programming language, documentation system, and system for advanced connectivity to other applications), both of which are made commercially available by Wolfram Research, Inc.

Sometimes such curves are approximated using double reflection via two reflecting curves. For example, there can be a parabaloid nearer to and initially receiving a x-rays from anode 106, and a hyperboloid receiving x-rays reflected off the parabaloid curve.

Figure 4B:
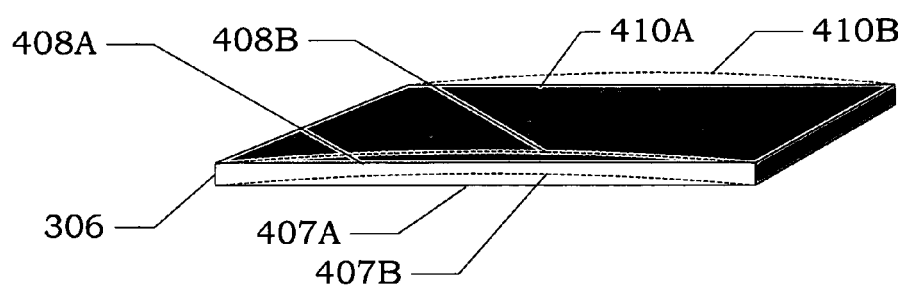
FIG. 4B is a perspective side view of the shim of FIGS. 3A-3D, according to at least one embodiment of the present invention.

FIG. 4B is a perspective side view of shim 306, according to at least one embodiment of the present invention. Front bottom edge 407A, front upper edge 408A, rear upper edge 410A and the corresponding rear lower edge (not depicted in FIG. 4B) can be straight (or substantially straight) surfaces where reflector 320 has straight (or substantially straight) side edges. Alternatively, where the side edges of reflector 320 are curved (again, to be discussed further below), then front bottom edge 407B, front upper edge 408B, rear upper edge 410B and the corresponding rear lower edge (not depicted in FIG. 4B) can take on a corresponding curved configuration. It is noted that front bottom edge 407A, front upper edge 408A, rear upper edge 410A and the corresponding rear lower edge can be parallel (or substantially parallel).

Figure 5:
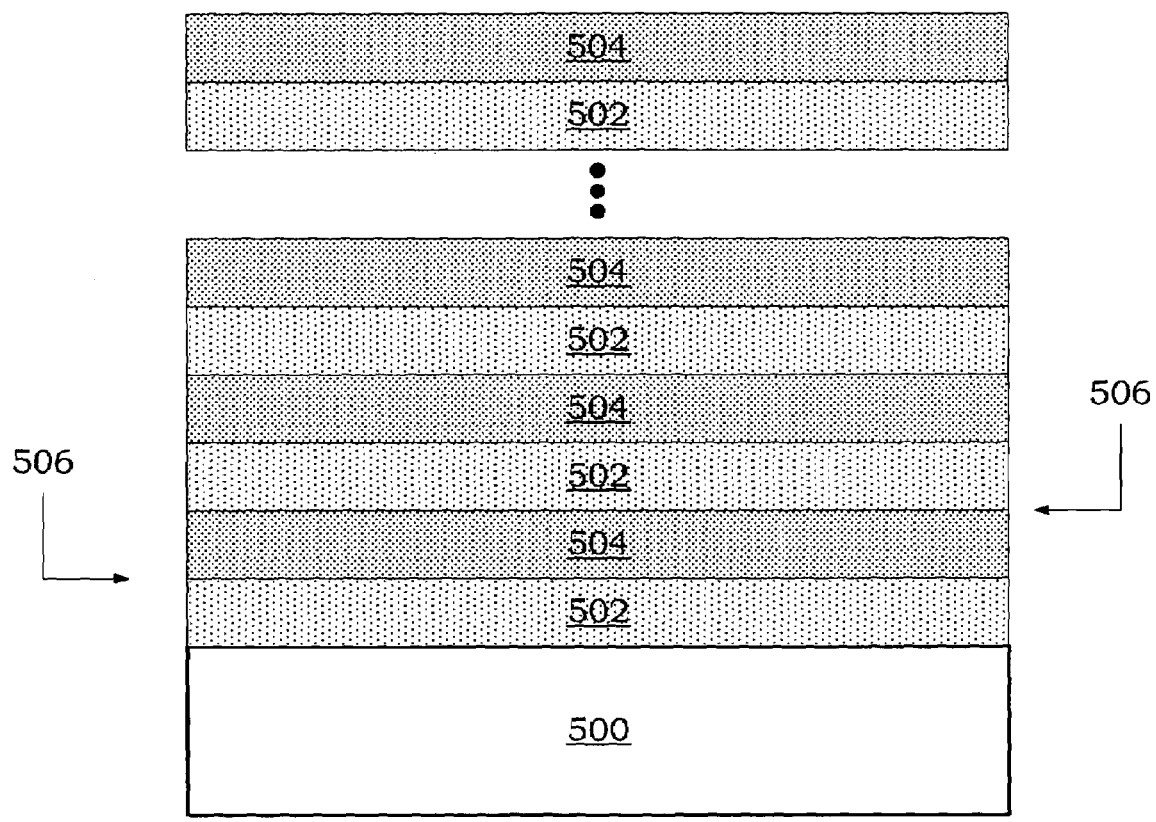
FIG. 5 is a cross section of the reflector of FIGS. 3A-3D, according to at least one embodiment of the present invention.

FIG. 5 is a cross section of reflector 320, according to at least one embodiment of the present invention. FIG. 5 is taken from the same perspective as FIG. 3C. General manufacture of reflectors, e.g., mirrors, in the art of x-ray telescopy is known. In FIG. 5, reflector 320 includes: a structural substrate 500, e.g., a metal such as aluminum (AL) or glass (the latter exhibiting smoother surface); a first layer 502 of heavy Z metal, e.g., gold (Au), platinum (Pt) and/or iridium (Ir) formed on substrate 500; and a first layer of carbon (C) 504, e.g., pure carbon, formed on the first metal layer 502. An interface between metal layer 502 and carbon layer 504 defines a reflecting surface 506. Multiple pairs of metal layer 502 and carbon layer 504 are stacked one on the other in a typical reflector 320. For example, the number of such stacked pairs can be in a range of 2-200.

Figure 6:
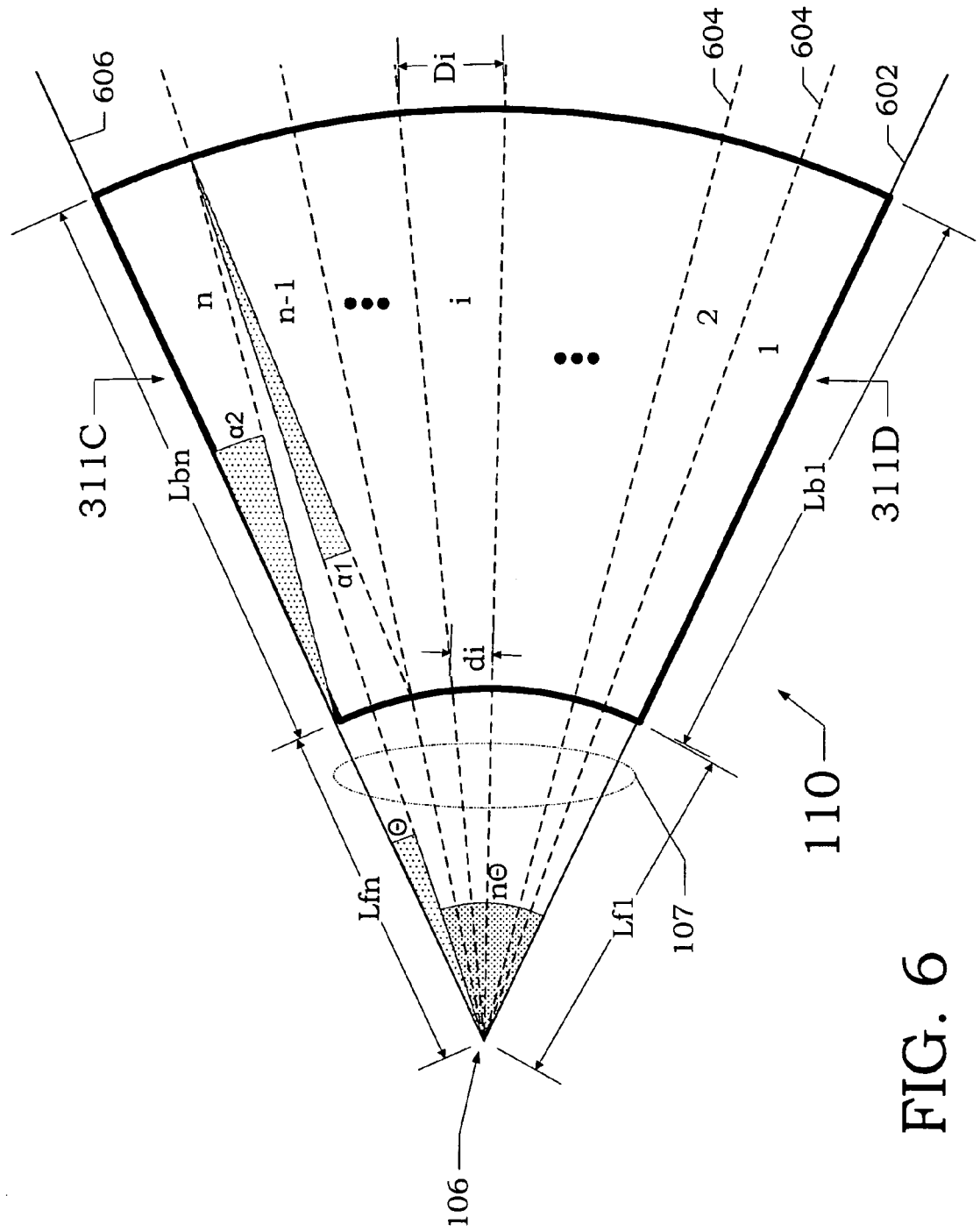
FIG. 6 is a side view of a portion the broad band x-ray beam of FIG. 1 with a side view of the filter (similar to the cross-sectional view depicted in FIG. 3A) superimposed thereon, annotated to describe a method of determining a shape of the filter, according to at least one embodiment of the present invention.

FIG. 6 is a side view of a portion of broad band x-ray beam 107 with a side view of filter 110 (similar to the cross-sectional view depicted in FIG. 3A) superimposed thereon, annotated to describe a method of determining a shape of filter 110, according to at least one embodiment of the present invention. In FIG. 6, rays 602, 604 and 606 are depicted. The radial planes mentioned in regard to FIG. 3A would be described as perpendicular to the page on which FIG. 6 is printed, with the results that rays 602, 604 and 606 would be described as lying in the radial planes, respectively, and the common origin would be located at source 106. Generally, the mathematics to determine a configuration of an x-ray reflector for the production of a narrow band x-ray beam are known. In FIG. 6, the term θ is the resolution of narrow band x-ray beam 112 for each reflector 320, where θ=α2−α1. Filter 110 includes n reflectors 320, for a total resolution of nθ.

The term α1 represents the minimum angle of reflection needed to generate the desired narrow band of x-rays. The term α2 represents the maximum angle of reflection needed to generate the desired narrow band of x-rays. The term n represents the number of reflectors 321 being used.

One of the equations for energy, which relates energy to frequency, is to be recalled.

$$E = \hbar\omega = \hbar\frac{2\pi}{f} \qquad (3)$$

where

E is energy;

$\hbar$ is Planck's constant;

ω is angular frequency; and f is frequency.

Bragg's law for constructive reflection also is to be recalled.

$$2d*\sin\theta = n\lambda = \frac{nc}{f} \qquad (4)$$

where d is the thickness of the layer (e.g., of heavy Z metal) off which the x-ray is to be reflected;

λ is the wavelength of the x-ray;

n is any integer number; and c is the speed of light.

According to Bragg's law, for a given λ and d, it is possible to adjust θ to achieve a desired center frequency of narrow band x-ray beam 112/113.

Basic trigonometry derives the following.

$$Lbi = \frac{di}{\sin\theta} \qquad (5)$$

$$di = Lbi*\sin\alpha 1 \qquad (6)$$

where

Lbi is the focal length from anode 106 to front surface 312 of filter 110 for reflector 320-i; and di is an approximation of the length of the arc segment of front surface 312 swept out by angle θ for the first reflector 320-1.

Basic trigonometry also derives the following.

$$Lfi = \left(\frac{1}{\sqrt{(1+\tan^2\theta)^{i-1}}}\right)*Lf1 \qquad (7)$$

Basic trigonometry also derives the following.

$$Di \approx Lbi*\sin\theta \qquad (8)$$

and $$Di = \left(\frac{1}{\sqrt{(1+\tan^2\theta)^{i-1}}}\right)*D1 \qquad (9)$$

and, for small values of θ, $$1 \approx \left(\frac{1}{\sqrt{(1+\tan^2\theta)^{i-1}}}\right) \qquad (10)$$

hence, $$Di \approx D1 \qquad (11)$$

To summarize, appropriate selection of α1, α2 and n can obtain the desired center frequency of narrow band x-ray beam 112/113.

FIGS. 7A-7G are cross-sectional views (from the same perspective of FIG. 3C) that depict method, accordingly to at least one embodiment of the present invention, of constructing filter 110. The method of FIGS. 7A-7G incrementally builds up left & right frames (left & right stacks of spacers 304 and 306, plus corresponding portions of base 302 and top member 308) built up from discrete components. Again, this contrasts with the Background Art that uses upper and lower frames that are of integral formation.

Figure 7A:
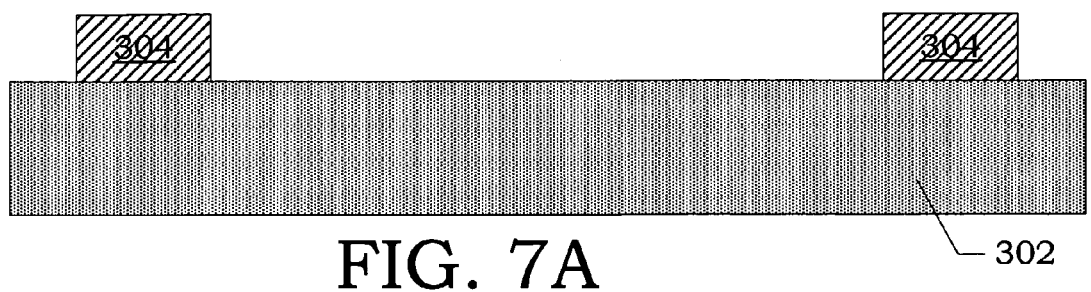
FIGS. 7A-7G are cross-sectional views (from the same perspective of FIG. 3C) that depict aspects of a method, accordingly to at least one embodiment of the present invention, of constructing the filter of FIG. 1.
Figure 7B:
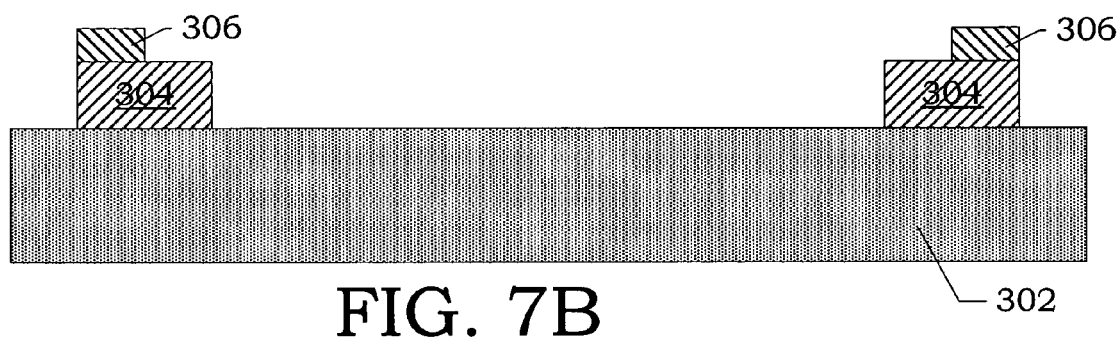
Figure 7C:
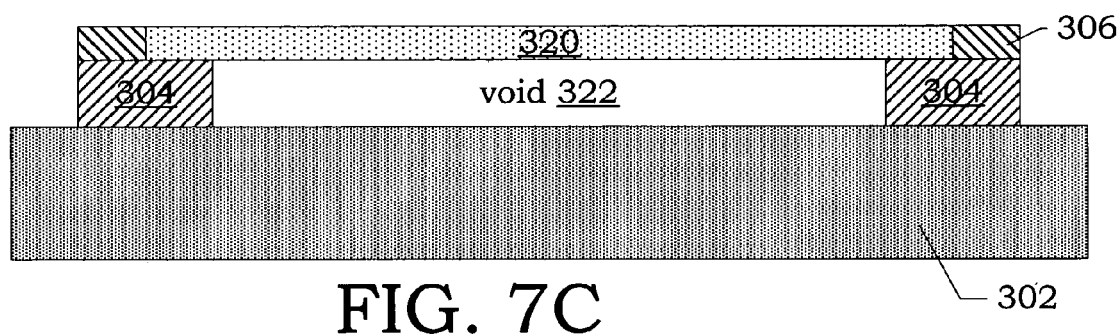

In FIG. 7A, base 302 is provided and then a first pair of first spacers 304 are disposed thereon. In FIG. 7B, a first pair of first shims 306 are disposed on outer edge areas of the upper surfaces of the first spacers 304. In FIG. 7C, a first reflector 320 is disposed on inner edge areas of the upper surfaces of the first spacers 304. The result is the completion of a first reflection unit 321 (not labeled in FIG. 7C, but see FIG. 3C).

Figure 7D:
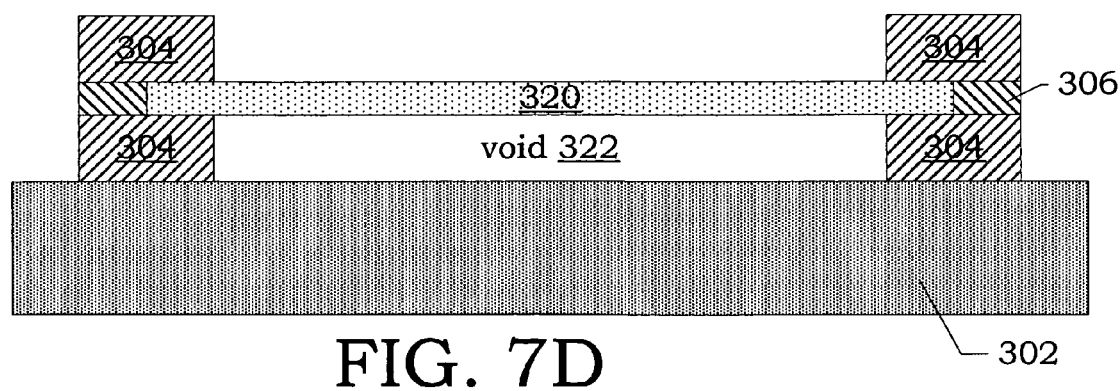

In FIG. 7D, a second pair of second spacers 304 are disposed on upper surfaces of the first shims 306. Outer edge areas of the lower surfaces of the second spacers 304 are located on the upper surfaces of the first shims 306. Inner edge areas of the lower surfaces of the second spacers 304 are disposed over, and may be in contact (as noted above) with outer edge areas of the upper surface of the first reflector 320.

Figure 7E:
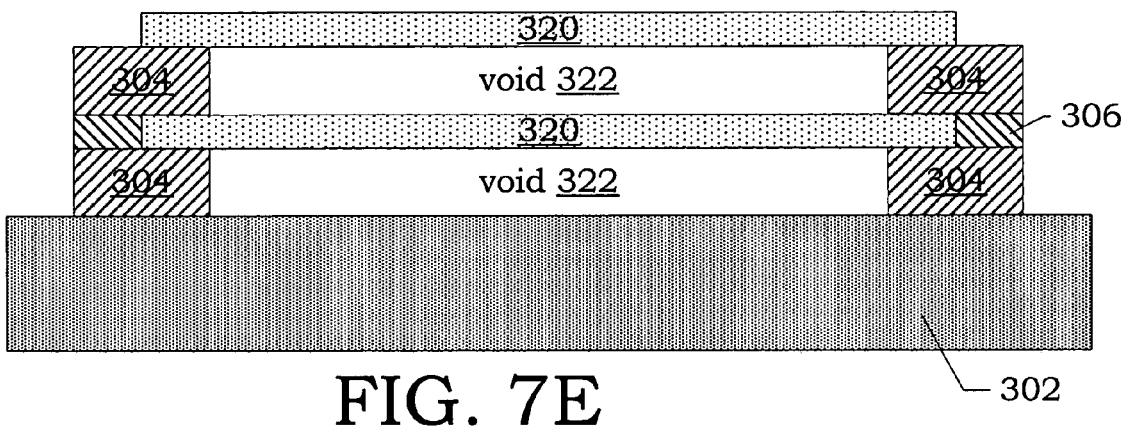
Figure 7F:
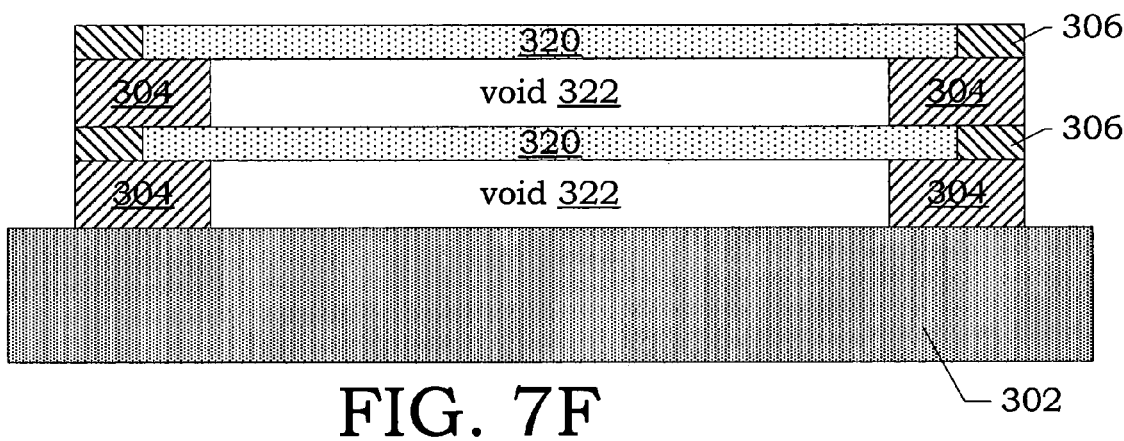

In FIG. 7E, a second reflector 320 is disposed on inner edge areas of the upper surfaces of the second spacers 304. In FIG. 7F, a second pair of second shims 306 are disposed on outer edge areas of the upper surfaces of the second spacers 304. The result is the completion of a second reflection unit 321 (not labeled in FIG. 7F, but again see FIG. 3C). It is noted that the sequence of FIGS. 7E-7F is opposite the sequence of FIGS. 7B-7C. This is merely to illustrate that the order in which shims 306 and reflector 320 are disposed onto the underlying spacers 304 is interchangeable. As a practical matter, an entire assembly of a filter 304 would probably preserve the sequence of FIGS. 7B-7C or FIGS. 7E-7F throughout.

Figure 7G:
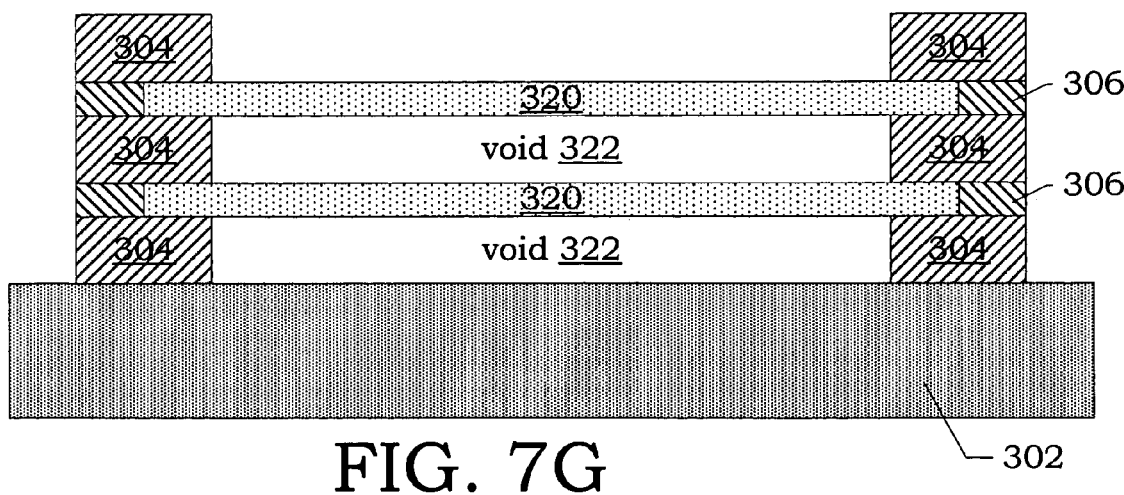

In FIG. 7G, a third pair of third spacers 304 is disposed on upper surfaces of the second shims 306. Construction continues in the manner described above until a sufficient number of reflection units is constructed, at which time top member 308 is disposed on the uppermost (or $n^{th}$) pair of shims 306.

Figure 8B:
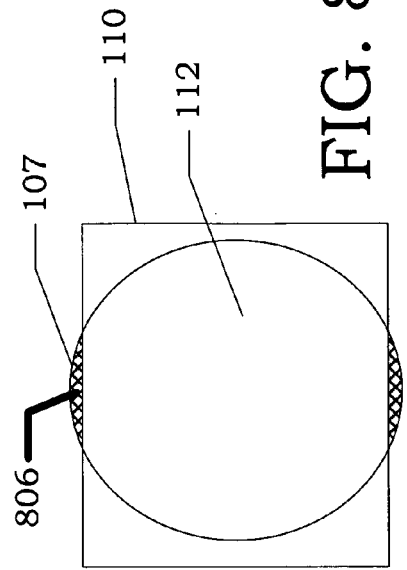
FIG. 8B is the corresponding cross-sectional view thereof.
Figure 8D:
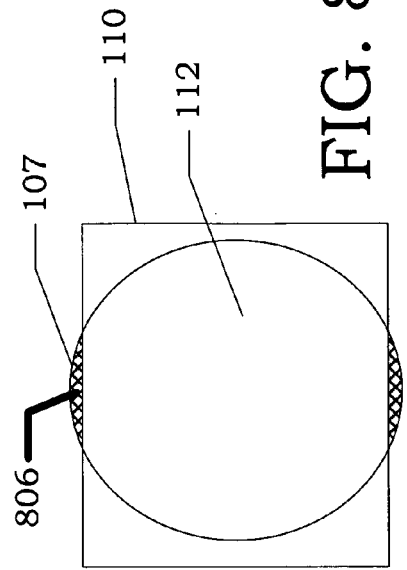
FIG. 8D is the corresponding cross-sectional view thereof.
Figure 8A:
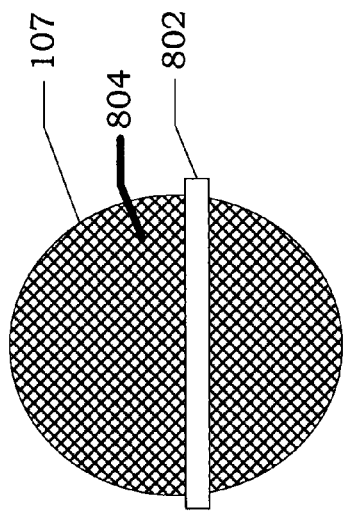
Figure 8C:
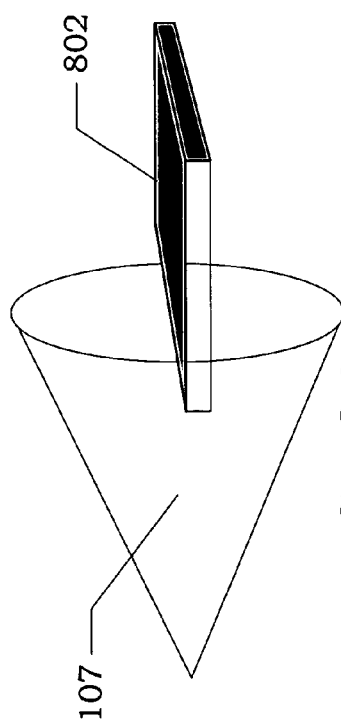

FIG. 8A is a simplified perspective side view of the Background Art narrow band x-ray filter 802, while FIG. 8B is the corresponding cross-sectional view thereof depicted from the perspective of looking into the wide end of broad band beam 107 as if looking past filter 802 toward anode 106. FIG. 8C is a simplified perspective side view of narrow band x-ray filter 110 (again, according to at least one embodiment of the present invention). filter, while FIG. 8D is the corresponding cross-sectional view thereof depicted from the perspective of looking into the wide end of broad band beam 107 as if looking past filter 110 toward anode 106.

Background Art filter 802 can only accommodate a thin slice of the cross-section of broad band x-ray beam 107. As a result, only that thin slice is transformed into a narrow band x-ray beam. Most of broad band x-ray beam 107 is wasted, as indicated by a large cross-hatched area 804 in FIG. 8B.

In contrast, filter 110 can accommodate at least a majority of the cross-section of broad band x-ray beam 107, if not substantially the entirety thereof. As a result, at least a majority (if not substantially the entirety) of the cross-section of broad band x-ray beam 107 is transformed into narrow band x-ray beam 112. In other words, a much smaller (if not substantially negligible) portion of broad band beam 107 is wasted, as indicated by cross-hatched area 806. While a system that uses Background Art filter 802 would have to repeatedly scan subject 116 in order to obtain a complete image, system 100 (that uses filter 110) can obtain a complete image in many fewer scans, a lower limit being as few as only one scan, which is significantly faster.

As contrasted with the Background Art, x-ray radiology system 100/200 can be used in a medical circumstance to achieve sharper and higher x-ray images that exhibit improved contrast between, e.g., normal tissue and cancerous tissue, while exposing subject/patient 116 to a relatively lower radiation dosage (about 90% less than a broad band x-ray beam exposure according to the Background Art). Moreover, the need for subject 116 to ingest an x-ray contrast agent, e.g., barium (Ba) or iodine (I), can be reduced relative to the Background Art. Narrow band x-ray beam 112/113 can be adjusted to exhibit center frequencies that are most useful for medical imaging. Cancer tumors at least as small as 0.2 mm-0.3 mm can be detected with such systems. This can lead to earlier diagnosis of disease, which increases the chances of saving lives.

An advantage to using both of systems 100 and 200 in a medical circumstance is that the narrow band x-ray beam exposure minimizes radiation exposure otherwise suffered by subject 116 imaged according to the Background Art with by a corresponding system that only forms the image only with broad-band x-ray beam exposure. Moreover, total exposure time can be reduced.

Where x-ray radiology system 100/200 is used in a security circumstance and subject 116 is a living organism, an x-ray image can be made in real-time a low dosage exposure to assess whether subject 116 has concealed a weapon or contraband in a body cavity.

The present invention being thus described, it will be obvious that the same may be varied in many ways. Such variations are not to be regarded as a departure from the spirit and scope of the present invention, and all such modifications are intended to be included within the scope of the present invention.

What is claimed is:

1. A narrow band x-ray filter comprising:
   a substrate; and
   a sheaf of one or more reflection units stacked upon each other on the substrate, each reflection unit including
   a first set of at least two discrete spacers on a respective underlying structure,
   a reflector disposed on the first set of spacers so as to form a void between the respective underlying structure and the reflector, and
   a first set of at least two discrete shims disposed on the first set of at least two spacers, each shim being at least substantially the same thickness as the reflector.

2. The filter of claim 1, wherein each reflector includes:
   a base layer; and
   a stack of one or more mirrors, each mirror including
   a heavy Z metal layer, and
   a layer of carbon on the metal layer.

3. The filter of claim 2, wherein the heavy Z metal includes at least one of gold, platinum and iridium.

4. The filter of claim 3, wherein each stack includes 2-200 mirrors.

5. The filter of claim 1, wherein the filter further includes a top member on the sheaf.

6. The filter of claim 1, wherein the sheaf includes between 2 and 300 reflection units.

7. An apparatus, to produce a substantially narrow band x-ray beam; the apparatus comprising:
   a source of a first x-ray beam; and
   a narrow band x-ray filter having a first end, a second end and a focal point located nearer to the first end than to the second end, and
   the source being disposed substantially at the focal point such that a substantially narrow band x-ray beam emanates from the second end of the filter; and
   the filter being configured and disposed so as to receive at the focal point at least a majority of the cross-section of the first x-ray beam;
   wherein the filter includes the following,
      a substrate, and
      a sheaf of one or more reflection units stacked upon each other on the substrate, each reflection unit including the following,
         a first set of at least two discrete spacers on a respective underlying structure,
         a reflector disposed on the first set of spacers so as to form a void between the respective underlying structure and the reflector, and
         a first set of at least two discrete shims disposed on the first set of at least two spacers, each shim being at least substantially the same thickness as the reflector.

8. The apparatus of claim 7, wherein the filter is configured and disposed so as to receive at the focal point substantially the entire cross-section of the first band x-ray beam.

9. The apparatus of claim 7 wherein the filter is an X-ray telescope such that the narrow band x-ray beam is formed of substantially parallel x-rays.

10. The apparatus of 7, wherein the narrow band x-ray beam is formed of x-ray that diverge from the second end of the filter.

11. The apparatus of claim 7, wherein each reflector includes:
    a base layer; and
    a stack of one or more mirrors, each mirror including the following,
    a heavy Z metal layer, and
    a layer of carbon on the metal layer.

12. The apparatus of claim 7, wherein: the filter is movable in at lease one dimension; and the apparatus further comprises an adjustment unit to move the filter in the at least one dimension.

13. The apparatus of claim 7, wherein the first x-ray beam is a broad band x-ray beam.

14. An apparatus to make an x-ray image of a subject, the apparatus comprising:
- a source of a first x-ray beam; and
- a narrow band x-ray filter having a first end, a second end and a focal point located nearer to the first end than to the second end,
- the source being disposed substantially at the focal point such that a substantially narrow band x-ray beam emanates from the second end of the filter, and
- the filter being configured and disposed so as to receive at the focal point at least a majority of the cross-section of the first x-ray beam;
- an x-ray detector arranged to receive the narrow band x-ray beam so that a subject disposed between the second end of the filter and the detector casts an image thereon;
- wherein the filter includes the following,
  - a substrate, and,
  - a sheaf of one or more reflection units stacked upon each other on the substrate, each reflection unit including the following,
    - a first set of at least two discrete spacers on a respective underlying structure,
    - a reflector disposed on the first set of spacers so as to form a void between the respective underlying structure and the reflector,
    - a first set of at least two discrete shims disposed on the first set of at least two spacers, each shim being at least substantially the same thickness as the reflector,
    - each reflector including a base layer, and
    - a stack of one or more mirrors, each mirror including the following,
      - a heavy Z metal layer, and
      - a layer of carbon on the metal layer.

15. A method of making a narrow band x-ray filter, the method comprising;
- providing a substrate; and
- stacking two or more reflection units in succession upon the substrate such that the two or more reflection units are aligned according to a plurality of radial planes that share a common origin, respectively;
- wherein the step of stacking, for each reflection unit, the following,
  - disposing a first set of at least two discrete spacers on a respective underlying structure,
  - disposing a reflector on the first set of spacers so as to form a void between the respective underlying structure and the reflector, and
  - disposing a first set of at least two discrete shims on the first set of at least two spacers, each shim being at least substantially the same thickness as the reflector.

16. The method of claim 15, further comprising:
- mechanically connecting the two or more successively-stacked units to the substrate so as to form a sheaf of reflection units.

17. The method of claim 15, wherein each reflector includes:
- a base layer; and
- a stack of one or more mirrors, each mirror including
  - a heavy Z metal layer, and
  - a layer of carbon on the metal layer.

18. The method of claim 17, wherein the heavy Z metal includes at least one of gold, platinum and iridium.

19. The method of claim 17, wherein each reflector includes 2-200 mirrors.

20. The method of claim 15, further comprising:
- disposing a top member on the sheaf.

21. The method of claim 15, wherein the sheaf includes between 2 and 300 reflection units.

22. The method of claim 15, wherein the step of stacking, for each reflection unit, includes:
- disposing a first set of at least two rails on a respective underlying structure, and
- disposing a reflector on the first set of rails so as to form a void between the respective underlying structure and the reflector.

23. The method of claim 22, wherein:
- the step of stacking further includes the following,
  - configuring each rail to exhibit, in cross section, a shape resembling a staircase including at least first and second steps;
- a first step portion of the rail, being located relatively upward from the respective underlying structure, corresponds to a first surface upon which the reflector is disposed; and
- a second step portion of the rail corresponds to a second surface which can support another rail disposable thereon.

24. The method of claim 15, wherein the step of stacking includes orienting each reflection unit such that leading edges of the reflection units are subjected to substantially the same angle of incidence with respect to a source of x-rays located at the common origin.

* * * * *